United States Patent [19]
Rees et al.

[11] Patent Number: 5,972,332
[45] Date of Patent: Oct. 26, 1999

[54] WOUND TREATMENT WITH KERATINOCYTES ON A SOLID SUPPORT ENCLOSED IN A POROUS MATERIAL

[75] Inventors: Riley S. Rees; Cynthia Marcelo; Belinda Adamson; Lenore Rhodes; Beverly Marchant, all of Ann Arbor; William Lindblad, Farmington; Robert Gilmont, Ann Arbor; Warren Garner, Ann Arbor; Cynthia Zuccaro, Dexter; Thomas E. Taddonio, Manchester, all of Mich.

[73] Assignee: The Regents of the University of Michigan, Ann Arbor, Mich.

[21] Appl. No.: 08/840,804

[22] Filed: Apr. 16, 1997

[51] Int. Cl.[6] .............................. C12N 5/00; C12N 11/04; A01N 63/00; A61F 13/00
[52] U.S. Cl. ..................... 424/93.7; 424/422; 435/177; 435/180; 435/182; 435/382; 435/395; 435/402
[58] Field of Search ................................. 435/395, 402, 435/403, 382, 177, 180, 182; 424/93.7, 422

[56] References Cited

U.S. PATENT DOCUMENTS

| | | | |
|---|---|---|---|
| 4,576,715 | 3/1986 | Michaels et al. | 210/347 |
| 4,997,443 | 3/1991 | Walthall et al. | 623/11 |
| 5,269,917 | 12/1993 | Stankowski | 210/232 |
| 5,459,069 | 10/1995 | Palsson et al. | 435/289.1 |
| 5,487,889 | 1/1996 | Eckert et al. | 424/93.1 |
| 5,512,474 | 4/1996 | Clapper et al. | 435/240.243 |
| 5,563,068 | 10/1996 | Zhang et al. | 435/295.2 |
| 5,643,773 | 7/1997 | Aebischer et al. | 435/182 |
| 5,693,332 | 12/1997 | Hansbrough | 424/426 |
| 5,712,163 | 1/1998 | Parenteau et al. | 435/405 |
| 5,741,685 | 4/1998 | Vacenti | 435/182 |
| 5,830,507 | 11/1998 | Armstrong | 424/489 |

FOREIGN PATENT DOCUMENTS

WO8803785  6/1988  WIPO.

OTHER PUBLICATIONS

Davies J.W.L., Burns, 10:94–103 (1983).
Hansbrough et.al., J. Burn Care Rehabil., 14:485–94 (1993).
Hansbrough et.al., J. Am. Med. Assoc., 262:2125–2130 (1989).
Ronfard et.al., Burns, 17:181–184 (1991).
Marchahal et al., Brit. J. Plas. Surg., 45:354–363 (1992).
Carver et.al., Brit. J. Plas. Surg., 46:228–234 (1993).
Green et.al., Proc. Nat. Acad. Sci., 76:5665–5668 (1979).
Jones et.al., J. Surg. Res., 51:344–352 (1991).

*Primary Examiner*—David M. Naff
*Attorney, Agent, or Firm*—Medlen & Carroll, LLP

[57] ABSTRACT

Devices and methods for enhancing the healing of wounds, especially chronic wounds (e.g., diabetic wounds), are provided involving the use of keratinocytes. Keratinocytes are grown on a transplantable solid support (e.g., collagen-coated beads), and the keratinocyte-coated solid support is placed in an enclosure. The enclosure, in turn, is placed in the wound for use as an interactive wound healing promoter. After the enclosure is placed in a wound, the wound may be covered with a dressing. The enclosure is degradable or non-degradable, and is constructed from a membrane or a porous polyester mesh material having pores that are either too small or large enough for keratinocytes to cross. A means may be attached to the enclosure to enable removing the enclosure from a wound.

6 Claims, 1 Drawing Sheet

WOUND TREATMENT WITH KERATINOCYTES ON A SOLID SUPPORT ENCLOSED IN A POROUS MATERIAL

FIELD OF THE INVENTION

The present invention relates generally to tissue healing and regeneration and, more particularly, to methods and systems for wound healing.

BACKGROUND OF THE INVENTION

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age [see Hunt and Goodson in *Current Surgical Diagnosis & Treatment* (Way; Appleton & Lange), pp. 86–98 (1988)].

Wounds which do not readily heal can cause the subject considerable physical, emotional, and social distress as well as great financial expense [see, e.g., Richey et al., Annals of Plastic Surgery 23(2):159–165 (1989)]. Indeed, wounds that fail to heal properly and become infected may require excision of the affected tissue. A number of treatment modalities have been developed as scientists' basic understanding of wounds and wound healing mechanisms has progressed.

The most commonly used conventional modality to assist in wound healing involves the use of wound dressings. In the 1960s, a major breakthrough in wound care occurred when it was discovered that wound healing with a moist occlusive dressings was, generally speaking, more effective than the use of dry, non-occlusive dressings [Winter, Nature 193:293–94 (1962)]. Today, numerous types of dressings are routinely used, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, Dermatol. Surg. 21:583–590 (1995); Davies, *Burns* 10:94 (1983)]. Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, treatment regimens involving zinc sulfate have been utilized by some practitioners. However, the efficacy of these regimens has been primarily attributed to their reversal of the effects of sub-normal serum zinc levels (e.g., decreased host resistance and altered intracellular bactericidal activity) [Riley, Am. Fam. Physician 24:107 (1981)]. While other vitamin and mineral deficiencies have also been associated with decreased wound healing (e.g, deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

What is needed is a safe, effective, and interactive means for enhancing the healing of chronic wounds. The means should be able to be used without regard to the type of wound or the nature of the patient population to which the subject belongs.

SUMMARY OF THE INVENTION

The present invention is directed at systems and methods for enhancing the healing of wounds, especially chronic wounds (e.g., diabetic wounds, pressure sores), involving the use of cultured keratinocytes. In some embodiments, the invention contemplates the use of keratinocytes grown on a transplantable solid support. The present invention is not limited by the nature of the solid support; indeed, the present invention contemplates the use of any three-dimensional support or matrix (e.g., matrices comprised of glycosaminoglycans) to which keratinocytes will adhere, divide, and maintain their functional behaviors (e.g., heal wounds).

In preferred embodiments, the solid support comprises collagen-coated beads. In particular embodiments, the collagen-coated beads are placed in an enclosure, compartment, bag, or similar barrier, said enclosure having pores, and the enclosure is then placed at the wound site for use as an interactive wound healing promoter. The present invention is not limited by the nature of enclosure; however, in one embodiment, the pores are large enough to permit the cells from the beads to exit the enclosure into the wound, while in another embodiment, the pores are too small to permit cells from the beads to exit the enclosure, but large enough to permit cellular factors to exit the enclosure or wound fluid components to enter the enclosure. In certain embodiments, the enclosures are replaced every few days until the wound heals.

More particularly, the present invention contemplates a system for the treatment of wounds, comprising a) keratinocytes on a solid support; and b) an enclosure, the enclosure housing the solid support. In some embodiments, the solid support comprises beads, and in further embodiments, the beads are macroporous. In still further embodiments, the beads are coated with an extracellular matrix (e.g., collagen). While the present invention is not limited to the nature of the keratinocytes, in a preferred embodiment the keratinoctes are viable and growing.

In additional embodiments, the enclosure comprises a mesh material, having pores. In certain embodiments, the mesh material comprises polyester. In one embodiment, the pores are large enough to permit the cells from the beads to exit the enclosure into the wound, while in another embodiment, the pores are too small to permit cells from the beads to exit the enclosure, but large enough to permit cellular factors (e.g., cytokines) to exit the enclosure or wound fluid components to enter the enclosure.

Moreover, in further embodiments, the enclosure comprises a biocompatible membrane. In additional embodiments, the enclosure comprises means for removing the enclosure from a wound. In particular embodiments, the removal means comprises a handle or string attached to the enclosure.

The present invention also contemplates a method for treating a wound, comprising a) providing: i) keratinocytes on a solid support, ii) an enclosure, and iii) a subject having a least one wound; b) placing the keratinocyte-containing solid support into the enclosure so as to produce a keratinocyte-containing enclosure; and c) positioning the keratinocyte-containing enclosure in the wound of the subject under conditions such that the healing of the wound is promoted. Additional embodiments further comprise, after step b) and prior to step c), sealing the enclosure to produce a sealed keratinocyte-containing enclosure. Finally, some embodiments further comprise step d), covering the wound containing the keratinocyte-containing enclosure with a dressing.

DEFINITIONS

To facilitate understanding of the invention set forth in the disclosure that follows, a number of terms are defined below.

The term "wound" refers broadly to injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I–III; examples of partial thickness wounds include burn wounds, pressure sores, venous stasis ulcers, and diabetic ulcers. The term "deep wound" is meant to include both Grade III and Grade IV wounds.

The term "chronic wound" refers to a wound that has not healed within 30 days.

The phrase "positioning the enclosure in the wound" is intended to mean contacting some part of the wound with the enclosure. "Containing" includes, but is not limited to, bringing the enclosure proximate to the wound so as to bring the cells in fluidic communication with the wound.

The phrases "promote wound healing," "enhance wound healing," and the like refer to either the induction of the formation of granulation tissue of wound contraction and/or the induction of epithelialization (i.e., the generation of new cells in the epithelium).

The phrase "wound fluid contents" refers to liquid associated with a wound, as well as cells, cell factors, ions, macromolecules and protein material suspended such liquid at the wound site.

The term "keratinocyte" refers to cells that produce keratin (ceratin), a scleroprotein or albuminoid. Generally speaking, keratinocytes are found in the epidermis or from cell lines derived from keratinocytes (e.g., bacterial derived products).

The term "subject" refers to both humans and animals.

The terms "enclosure," "compartment," and the like refer broadly to any container capable of confining a cell-coated solid support within a defined location while allowing cellular factors to exit the enclosure into the wound and wound fluid contents to enter. In preferred embodiments, the enclosure is a sterile mesh pouch constructed of a woven, medical-grade polyester mesh. In one embodiment, the present invention contemplates a degradable enclosure (i.e., an enclosure that breaks down over time). In addition, the present invention contemplates the use of an enclosure constructed from membranes. Preferably, after the solid support containing cells (e.g., growing on the surface of the solid support or within the solid support) is placed within the enclosure, the enclosure is sealed so as to prevent the solid support from exiting the enclosure. In one embodiment, the sealed enclosure further comprises a transport means for transporting cellular factors (e.g., outside of the enclosure and into the wound). While the present invention is not limited to a particular transport means, the transport means can include a means for applying pressure (e.g., a pump).

The term "solid support" refers broadly to any support that allows for cell growth, including, but not limited to, microcarrier beads, gels, and culture plate inserts. Microcarrier beads suitable for use with the present invention are commercially-available from a number of sources, including Sigma, Pharmacia, and ICN. In preferred embodiments, the keratinocytes are grown on collagen-coated beads (e.g., CYTOLINE 1™ macroporous microcarrier beads (Pharmacia Biotech)). Culture plate inserts (i.e., cell support matrices that generally comprise a membrane that supports cell growth) are commercially available from, among other sources, Collaborative Biomedical Products, Costar, ICN, and Millipore. In preferred embodiments, the culture plate inserts comprise a permeable microporous membrane that allows free diffusion of ions and macromolecules.

The term "transplantable solid support" refers to a solid support containing cells (e.g., keratinocytes, referred to as a "keratinocyte-containing solid support") that can be placed within an enclosure. The enclosure containing the cell-containing solid support may then be placed in a wound to promote wound healing.

The phrases "means for removing," "removal means," and the like refer broadly to any mechanism useful for assisting in the withdrawal of a cell-containing enclosure from a wound (and/or the placement of the cell-containing enclosure within a wound). In some embodiments, the removal means comprises a string, thread, cord, or the like that is attached to the enclosure; in preferred embodiments, the removal means is attached to a grasp that can be used as a handle to assist in the placement of the solid support-containing enclosure within the wound and its removal therefrom.

The term "dressing" refers broadly to any material applied to a wound for protection, absorbance, drainage, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, Dermatol. Surg. 21:583–590 (1995); Davies, *Burns* 10:94 (1983)]. The present invention also contemplates the use of dressings impregnated with pharmacological compounds (e.g., antibiotics).

The term "biocompatible" means that there is minimal (ie., no significant difference is seen compared to a control), if any, effect on the surroundings. For example, in some embodiments of the present invention, the enclosure comprises a biocompatible membrane; the membrane itself has a minimal effect on the cells of the solid support (i.e., it is non-toxic and compatible with keratinocyte growth) within the membrane and on the subject (i.e., it has no adverse impact on the subject's health or the rate of wound healing) after the enclosure is placed into a wound.

The term "extracellular matrix" refers broadly to material for supporting cell growth. It is not intended that the present invention be limited by the particular material; the present invention contemplates a wide variety of materials, including, but not limited to, material that is distributed throughout the body of multicellular organisms such as glycoproteins, proteoglycans and complex carbohydrates. The present invention contemplates the use of a substratum of extracellular matrix with the culture inserts on which the cells (e.g., keratinocytes) are plated. Although the present invention is not limited by the nature of the extracellular matrix, the preferred extracellular matrices include Matrigel, Growth Factor Reduced Matrigel, fibrillar collagen, lamininn, fibronectin and collagen type IV. Collagen is the most preferred extracellular matrix for use with the present invention. However, the present invention is not limited to the use of collagen, nor to the use of solid supports that are commercially coated with collagen or other extracellular matrices.

DESCRIPTION OF THE DRAWING

The FIGURE diagrammatically depicts one embodiment of a tea bag contemplated for use with the cell-containing solid supports of the present invention. An enclosure, 1, is connects to a removal means, 2 and 3, and contains solid support, 4. In this embodiment, the removal means comprises a string, 2, and a tab connected to the string, 3.

DESCRIPTION OF THE INVENTION

Figure 1:
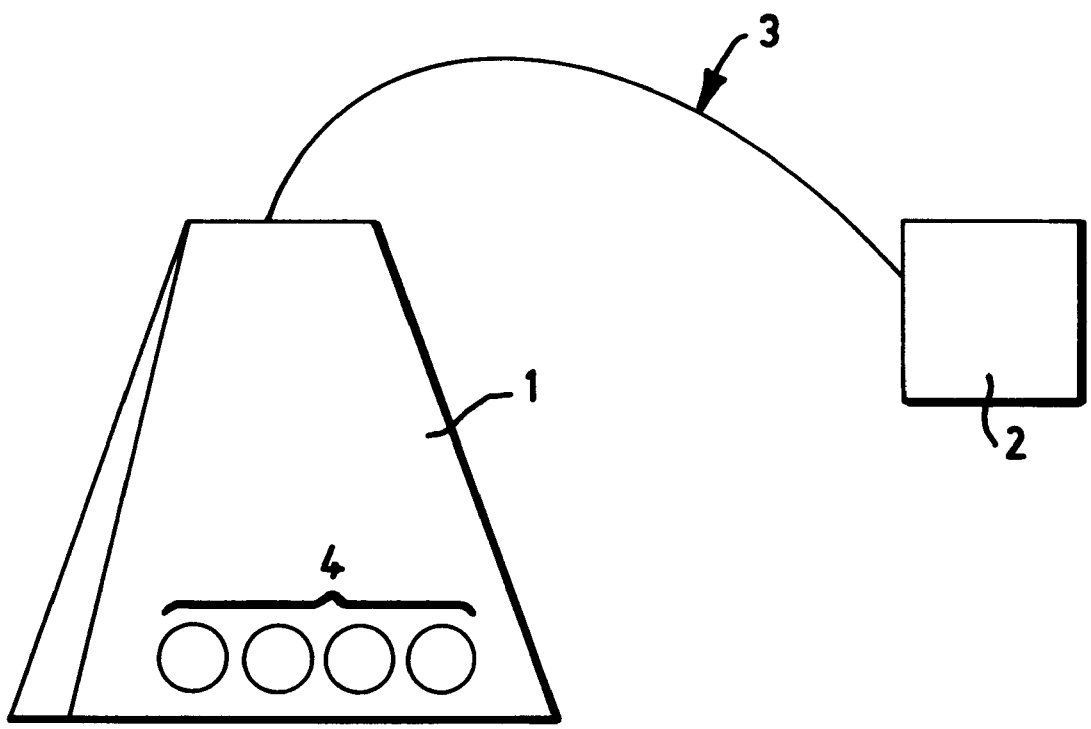

The present invention relates generally to tissue healing and regeneration and, more particularly, to methods and systems for wound healing.

The invention involves the unique use of cultured cells to treat wounds, especially chronic wounds (e.g., diabetic wounds). In preferred embodiments, cultured keratinocytes grown on transplantable solid supports are placed in a permeable enclosure; the enclosure is then placed in a wound. Though a precise understanding of how the cell-containing enclosure effects wound healing is not required in order to practice the present invention, it is believed that the cells in the enclosure secrete certain factors that enhance wound healing. The usefulness of the present invention has been demonstrated in athymic nude mice, an animal model routinely utilized in wound closure testing [see, e.g., Boyce et al., Surgery 110:866–76 (1991); Barbul et al., Surgery 105:764–69 (1989); and Hansbrough et al., J. Burn Care Rehabil. 14:485–94 (1993)].

The present invention is not limited by the nature of the cells utilized. Examples of cells include, but are not limited to, the cells set forth in Table I.

TABLE 1

| CELL TYPE | TISSUE | CYTOCKINE, GROWTH FACTOR, MADE/RESPONDS TO | MATRIX INTERACTIONS | WOUND HEALING POTENTIAL |
|---|---|---|---|---|
| Fibroblast | Dermis Viseral Organs | TGF-beta ,PDGF, IGF, IL-1, FGF, CTGF | Collagen type I, III, and IV, Elastin, Fibronectin, nidogen, SPARC, Osteonectin, Protenglycons, glucosamino-glycons, collagenases, gelatinase, stromelysin, TIMP, Thrombospondin | Fibroblast $^+4$ |
| Endothelial Cell | Blood Vessels | FGF, VEGF, Endothelin, IGF, IL-l | TIMP, GAG, Elastin, Laminin, Collagenase, Type IV Collagens Fibronectin | Endothelial Cell $^+4$ |
| Melanocyte | Dermis | IL-l, MSH | No ECM Production | Melanocyte $^+1$ |
| Smooth Muscle Cell | Blood Vessels | PGDG, IGF, EGF, FGF | TIMP, GAG, Elastin, Laminin, Collagenase, Collagens, Fibronectin | Smooth Muscle Cell $^+3$ |
| Fetal Fibroblast | Fetal Mesenchyma | FGF, TGF-beta , PDGF, ILGF, IL-l, FGF | TIMP, GAG, Elastin, Laminin, Collagenase, Collagens, Fibronectin | Fetal Fibroblast $^+3$ |
| Epithelial Cell | Dermis Mucosa | FGF, TGF-alpha, TGF-beta PDGF, IGF, IL-1 EGF, FGF, KGF IFN-gamma TNF-alpha, IL-1 alpha, activin | TIMP, GAG, Elastin, Laminin, Collagenase, Collagen type IV, VI, VII, laminins, Fibronectin, epillgrin, nidogen, elastin, tenascin, thrombospondin, GAGs, proteoglycons, EMMPRIN, SPARC, uPA, PAI, collagenase, gelatinase, stromelysin | Epithelial Cell $^+4$ |

ABBREVIATION GLOSSARY

| Cytokine, Growth Factors Made/Responds To | | Matrix Interactions | |
|---|---|---|---|
| TGF | Transforming Growth Factor | TIMP | Tissue Inhibitor of Metalloproteinases |
| PDGF | Platelet Derived Growth Factor | GAG | Glucose Aminoglycons |
| IGF | Insulin-like Growth Factor | SPARC | Secreted Protein Acidic and Rich in Cysteine |
| IL | Interleukin | ECM | Extracellular Matrix |
| FGF | Fibroblast Growth Factor | EMMPRIN | Extracellular Matrix Metalloproteinase Inducer |
| CTGF | Connective Tissue Growth Facor | uPA | Urokinase Type Plasminogen Activator |
| VEGF | Vascular Endothelial Growth Factor | PAI | Plasminogen Activator Inhibitor |
| MSH | Melanocyte Stimulating Hormone | | |
| EGF | Epidermal Growth Factor | | |
| KGF | Keratinocyte Growth Factor | | |
| IFN | Interferon | | |

I. Sources of Keratinocytes

The present invention is not limited by the source of the keratinocytes. In some preferred embodiments, the cells are obtained from living donors undergoing breast operations; prior to their use, the cells obtained from the donors are archived for at least six months, after which they are tested for the presence of viruses (e.g., hepatitis virus). In other preferred embodiments, the cells are cadaveric in origin. After the cells have been harvested from the cadaver, they are screened for viruses and other microbes prior to use.

Generally speaking, the keratinocytes contemplated for use with the present invention are primary cultured cells (i.e., the cells are not derived from cell lines) or are cells that have been transfected and developed into a keratinocyte derived cell line.

Example 1 in the Experimental section illustrates one embodiment of how keratinocytes may be isolated and processed for use with the present invention. However, it should be noted that the present invention is not limited to primary cultured cells.

Moreover, the present invention contemplates the use of cells that have similar characteristics to keratinocytes (e.g., cells that secrete growth factors, cytokines or keratin, whose behavior the cells utilize to promote wound healing). These cells may be derived, for example, from cells that are not keratinocytic in origin but have been modified by recombinant techniques.

II. Growth of Cells on Solid Supports

The cells contemplated for use with the present invention (e.g., keratinocytes) are grown on transplantable solid supports. The present invention contemplates the growth of keratinocytes on solid supports, including protein-coated solid surfaces, as has been described in the art. For example, Gilchrest et al. [Cell Bio Int. Rep. 4:1009 (1980)] describe the growth of keratinocytes on fibronectin-coated plates in the absence of a 3T3 monolayer, while Schafer et al. [Exp. Cell. Res. 183:112 (1989)] describe a study of keratinocytes on floating collagen gels. Furthermore, Cook and Buskirk [In Vitro Cell Dev. Biol. 31:132 (1995)] describe the growth of keratinocytes on a variety of matrices, including microporous membranes coated with collagen.

The present invention is not limited by the nature of the solid support. Indeed, the methods of the present invention may be practiced in conjunction with any support that allows for cell growth, including, but not limited to, microcarrier beads, gels, and culture plate inserts. When microcarrier beads are desired, suitable beads are commercially-available from a number of sources; for example, Sigma sells both collagen- and gelatin-coated beads, Pharmacia sells dextran-based beads, and ICN advertises collagen beads. In preferred embodiments, the keratinocytes are grown on collagen-coated beads (e.g., CYTOLINE 1™ macroporous microcarrier beads (Pharmacia Biotech)).

Furthermore, culture plate inserts (i.e., cell support matrices that generally comprise a membrane that supports cell growth) are commercially available from, among other sources, Collaborative Biomedical Products, Costar, ICN, and Millipore. Such inserts frequently comprise polyethylene terephthalate, polycarbonate, TEFLON® (Gore), and mixed cellulose esters. In particular embodiments, the culture plate inserts comprise a permeable microporous membrane that allows free diffusion of ions and macromolecules.

As indicated above, the present invention contemplates the use of transplantable solid supports. More specifically, the present invention contemplates the application of keratinocyte-coated solid supports, housed in an enclosure, to wounds. The use of cell-coated transplantable solid supports for application to wounds has been described in the art. For example, Hansbrough et al. [J. Am. Med. Assoc. 262:2125 (1989)] describe collagen-glycosaminoglycan membranes covered with keratinocytes for wound application. [See also, Cooper et al., J. Surg. Res. 48:528 (1990); Ronfard et al. Burns 17:181 (1991); Tinois et al., Exp. Cell Res. 193:310 (1991); and Nanchahal and Ward, Brit. J. Plas. Surg. 45:354 (1992)]. However, the enclosure of keratinocyte-coated solid supports has not been reported.

Generally speaking, growth of keratinocytes and other "anchorage-dependent" cells requires attachment to a surface and spreading out in order to grow. Conventionally, such cells have been cultured on the walls of non-agitated vessels (e.g, tissue culture flasks) and roller bottles [U.S. Pat. No. 5,512,474 to Clapper et al., hereby incorporated by reference]. Though not limited by the manner in which the keratinocytes are grown on the solid supports, the present invention contemplates the use of these conventional techniques for growing keratinocytes on solid supports (see Example 1).

Other techniques for culturing solid support-bound keratinocytes are contemplated for use with the present invention. In some embodiments, the present invention contemplates the use of bioreactors for cell growth [see U.S. Pat. No. 5,459,069 to Palsson et al. and U.S. Pat. No. 5.563,068 to Zhang et al., both hereby incorporated by reference]. Some bioreactors utilize hollow fiber systems. Frequently, bundles of parallel fibers are enclosed in an outer compartment; cells are grown on the outside surface of the fibers, while nutrient- and gas-enriched medium flows through the center of the hollow fibers, nourishing the cells [see, e.g., U.S. Pat. No. 5.512,474 to Clapper et al.].

In addition, bioreactors utilizing microcarriers (e.g., DEAE-derivatived dextran beads) can be used in conjunction with the present invention. In preferred embodiments, cell adhesion proteins like collagen, fibronectin, and laminin are used to anchor the cells to the solid support; collagen is the most preferred cell adhesion protein. Microcarriers may also incorporate an ionic charge to assist in cell attachment to the microcarrier. Frequently, the microcarriers are porous beads that are sufficiently large to allow cells to migrate and grow in the interior of the bead [see U.S. Pat. No. 5,512,474 to Clapper et al.].

In a particularly preferred embodiment, keratinocytes are supported on a rigid support matrix (a semipermeable membrane) which allows for cell adherence and growth. The cells form a dense, three-dimensional array with large surface area which enhances modification of the fluid phase bathing the cells; the cell-populated matrix is constantly exposed to wound fluid components which diffuse into the reactor. The fluid can be modified and/or the cells can secrete mediators into the fluid to optimize the wound environment.

III. Enclosures

The present invention contemplates the placement of keratinocyte-coated collagen beads in an enclosure, which, in turn, is placed in a wound. In preferred embodiments, the enclosure is a sterile mesh pouch constructed of a woven, medical-grade polyester mesh. Though not limited to mesh materials manufactured by any particular company, Tetko, Inc. and Saati currently manufacture mesh materials suitable for use with the present invention.

Of course, other suitable materials (e.g, nylon) may also be used and are within the scope of the present invention. Indeed, any material that exhibits biocompatibility when placed within a wound may be used with present invention. In addition, the present invention contemplates the use of an enclosure constructed from membranes, including the membranes sold commercially by Gelman Sciences and Millipore.

In a preferred embodiment, the enclosures are assembled as pocket-like containers with four edges and two surfaces. These containers may be manufactured in one of several ways. For example, the enclosure may be created by welding (ie., uniting to create a seal) two pieces of material (of approximately equal dimensions) together on three edges. The fourth edge is left open to allow filling of the enclosure with the keratinocyte-coated collagen beads.

In an alternative embodiment, the enclosure may be manufactured from one piece of material by first folding that piece of material back onto itself. The region where the material overlaps itself may then be welded, resulting in the formation of a cylindrical tube. Thereafter, a pocket can be formed by welding closed one of the open ends of the cylinder, leaving the other end open for filling with the keratinocyte-coated collagen beads; this enclosure design has the advantage of requiring one less weld.

The present invention is not limited to enclosures assembled as four-edged pockets nor is the invention limited to the techniques of constructing the enclosures disclosed above. For example, trapezoidal or circular enclosures may also be used in conjunction with the present invention.

For the assembly of the enclosures, the present invention contemplates the use of a variety of sealing techniques, including ultrasonic welding or heat welding. The technique of ultrasonic welding is well-known in the medical device-manufacturing art [see, e.g., U.S. Pat. Nos. 4,576,715 and 5,269,917, hereby incorporated by reference]. The present invention is not limited to a particular welding/sealing technique; indeed, any suitable sealing technique may be used with the present invention, including but not limited to ultrasonic, radiofrequency, heat, and impulse sealing.

In those embodiments comprising a mesh enclosure, the present invention is not limited by the pore size of the mesh. However, it should be noted that extremely small pores may retard or preclude the movement of materials out of the enclosure. The preferred range of pore sizes is from about 10 microns to about 300 microns. Likewise, if a membrane is used, the membrane must be permeable to the extent that it allow the cell factors to cross the membrane into the wound.

In preferred embodiments, the solid support-containing enclosures of the present invention are configured like tea-bags (see FIGURE). That is, one end of a handle (3) (e.g., a biocompatible nylon material or excess from a heat seal) is attached to the enclosure (1) housing the solid support (4), while the other end of the string is attached to a grasp (2). The grasp (2) is used as a "handle" to assist in the placement of the solid support-containing enclosure within the wound and its removal therefrom. The present invention is not limited by the material used to construct the grasp; in preferred embodiments, the grasp (2) comprises a medical grade polyester material. Generally speaking, the grasp (2) is taped to the subject's skin at a site external to the wound. The solid support (4) has cells (e.g., keratinocytes) attached; it is preferred that such cells are viable.

IV. Transfer of Cell Factors

Following placement of the enclosure within the wound, the cell factors (e.g., growth factors like epidermal growth factor, cytokines, PGDF, insulin like growth factor, TGF-beta, keratinocyte growth factor cytokine, TNF, chemokines, chemotactic peptides, tissue inhibitors of metalloproteinases, etc.) excreted from the keratinocytes pass through the enclosure and into the wound. The inventors of the present invention have found that it is not necessary for the keratinocytes to be in direct contact with the wound. Though an understanding of why such indirect contact is sufficient for wound healing is not required in order to practice the present invention, it is believed that the donor keratinocytes (i.e., those contained within the enclosure) create a favorable environment for growth of the keratinocytes present in the wound of the subject. Thus, the keratinocytes from the healed wound site are thought to be of recipient, rather than donor, origin [see Van der Merve et al., Burns 16:193 (1990)]. In addition, the keratinocytes may actively modify wound fluid characteristics or components (e.g., modulating protolytic activity to optimize the wound environment.

The inventors of the present invention discovered empirically that placement of keratinocyte-coated solid supports within the enclosures (described above) resulted in good "take" of ketatinecytes in deep wounds; in comparison, researchers previously reported less than ideal take in deeper wounds [Van der Merve et al., Burns 16:193 (1990)] when other techniques were used.

The inventors have found that the use of the present invention in conjunction with standard wound dressing materials does not adversely affect the ability to modify the wound environment. For example, after placing the keratinocyte-containing enclosures within a wound, the enclosures can itself be covered with occlusive dressings such as hydrogels, foams, calcium alginates, hydrocolloids, and films. Example 2 of the Experimental section addresses an embodiment wherein a keratinocyte-containing enclosure is covered by a wound dressing.

Experimental

The following examples serve to illustrate certain preferred embodiments and aspects of the present invention and are not to be construed as limiting the scope thereof.

In the experimental disclosure which follows, the following abbreviations apply: M (Molar); mM (millimolar); $\mu$M (micromolar); g (grams); mg (milligrams); $\mu$g (micrograms); kg (kilograms); L (liters); mL (milliliters); dL (deciliters); $\mu$L (microliters); cm (centimeters); mm (millimeters); $\mu$m (micrometers); nm (nanometers); h and hr (hours); min. (minutes); s and sec. (seconds); FDA (United States Food and Drug Administration); AET, Inc. (Middletown, Del.); Abbott (Abbott Laboratories, Chicago, Ill.); American International Electric Co. (Santa Fe Springs, Calif.); Collaborative Biomedical Products (Bedford, Mass.); Gelman Sciences (Ann Arbor, Mich.); ICN (ICN Biomedicals, Inc., Costa Mesa, Calif.); Jackson Labs (Bar Harbor, Me.); Labelon Corp. (Canadaigua, N.Y.); Labline (Melrose Park, Ill.); Mallinckrodt Veterinary (St Louis, Mo.); Millipore (Millford, Mass.); Pharmacia Biotech (Uppsala, Sweden); Richard-Allen, Inc. (Richland, Mich.); Saati (Stamford, Conn.); Sigma (St. Louis, Mo.); Tetko, Inc. (Depew, N.Y.); 3M Healthcare (St. Paul, Minn.); and Thunderware (Orinda, Calif.).

EXAMPLE 1

The experiments of this example demonstrate that human culture keratinocytes grown on macroporous microcarriers and contained in a porous enclosure improve healing in surgically created wounds in mice.

A. Experimental Methodology

Preparation of Human Keratinocytes
Isolation and Growing of Human keratinocytes

Human keratinocytes (AATB certified; University of Michigan cultured keratinocyte program) were isolated at The University of Michigan Burn/Trauma Unit from split thickness skin.

Trypsinization of the split thickness skin was effected as follows. The skin was placed dermis-side down in 150 mm Petri dishes. The pieces were cut into smaller pieces (about 2 cm×about 0.3 cm) and were soaked in a sterile solution of 30 mM HEPES, 10 mM glucose, 3 mM KCl, 130 mM NaCl, 1 mM $Na_2HPO_4$ buffer, pH 7.4 containing 50 units of Penicillin and 50 $\mu$g Streptomycin (Sigma, P-0906). After soaking for 1–2 hr at 4° C. the buffer was aspirated off, and 0.09% trypsin (Sigma, Type IX) in a Penicillin and Streptomycin buffer was added to the dishes containing the skin tissue.

After trypsinizing overnight at room temperature, the enzyme solution was aspirated off, and complete MCDB 153 (Gibco, Grand Island, N.Y.) medium containing trypsin inhibitor was added to the skin pieces. Complete MCDB 153 medium was made by supplementing basic MCDB 153 (Gibco, Grand Island, N.Y.) medium, prepared as described by Boyce and Ham ["Normal human epidermal keratinocytes," In *In Vitro Models for Cancer Research* (Weber and Sekely, eds.) CRC Press, Boca Raton, Fla., pp. 245–274 (1985)], with 0.6 $\mu$M (0.218 $\mu$g/mL) hydrocortisone, 5 ng/mL epidermal growth factor, 5 $\mu$g/mL insulin, 6% bovine pituitary extract, and 0.15 mM $CaCl_2$.

The dermis was separated from the epidermis, and the epidermal basal cells were gently scraped off both segments of the skin. The cell suspension was pooled into 50 mL conical centrifugation tubes, gently centrifuged at room temperature, and resuspended in 50 mL of complete medium plus 2% chelated serum.

The cells were counted using a hemacytometer, and $20 \times 10^6$ cells were plated into a T-75 Corning Plastic flasks and grown at 37° C. with 5% $CO_2$ gassing, using a humidified incubator. After 3 days, the used growth medium was removed and complete MCDB 153 without serum was added. The cells were fed every other day.

The cells were passaged during log phase of growth. Thereafter, the cells were trypsinized using 0.025% trypsin (type IX) plus 0.01% EDTA in the HEPES buffer. The monolayers were washed with the buffer twice, then 2–3 mL of freshly-made enzyme solution (or frozen aliquot) were added. After 1 min. at 37° C., the enzyme solution was gently aspirated off, and the cells were placed in flasks at 37° C. for 2–3 min. until the cell sheets came off the bottom with gentle tapping of the flask. The media was neutralized with 1–3 mL of MCDB 153 medium plus 0.03% trypsin inhibitor (Sigma). The cells were counted, centrifuged, and plated 0.5 to $1.0 \times 10^6$ cells per T-75 flask. Cells were passaged 3 to 4 times.

CYTOLINE 1™ Bead Wash

Five grams of CYTOLINE 1™ macroporous microcarrier beads (Pharmacia Biotech) were autoclaved for 10 min. in 40 mL Milli Q water (Millipore, Bedford, Mass.) in a 125 ml Erlenmeyer flask. Following the autoclaving procedures, the beads were cooled and the water was aspirated. The beads were re-suspended in 40 mL Milli Q water, and were then agitated at moderate speed on a Labline orbital shaker for 10 min. The water was again aspirated, and a final washing with 40 mL Milli Q water was performed.

The beads were transferred into a 50 mL conical culture tube, the water was aspirated, and 30 mL 0.1 N NaOH were added. The beads were incubated at room temperature overnight. The NaOH solution was aspirated off the beads, and the beads were resuspended in 50 mL Milli Q water. The aliquot was transferred to a 125 Erlenmeyer flask and shaken at moderate speed for ten minutes. The Milli Q water was aspirated off the beads, and the beads were resuspended in Milli Q water; this aspiration/resuspension procedure was repeated a total of five times. The pH was neutral (i.e., less than 8), as measured with pH paper.

The beads were aspirated and resuspended in 40 mL PBS without $Mg^{2+}$ and $Ca^{2+}$, and autoclaved 30 min. at 121° C.

Growth of Keratinocytes on CYTOLINE 1™ Beads

A slurry containing 10 mL of PBS solution and 5 g of beads (contained in a 50 mL sterile conical centrifuge tube) was autoclaved as described above. The PBS was decanted, and 50 mL of MCDB 153 complete medium was added to the beads. The cells were conditioned in the medium at 37° C. with 5% $CO_2$ gas for 48 hours.

The medium was decanted, and the beads were transferred into a separate 50 mL sterile centrifuge tube. Ten-to-15 mL of medium were added, and the suspension was centrifuged at 1000 rpm for 3 min. The medium was again decanted, and $30 \times 10^6$ breast cells (from a living donor passage 1, never frozen) were added. After gently agitating the cells with the beads for 5 minutes, the cells and beads were poured into a 250 mL glass roller bottle and 50 mL of medium was added; this was performed using a fermentor-agitated growth system.

As a toxicity assay, 5 mL of cells and beads were removed from the glass roller bottle and grown in a T-25 flask to determine the growth of the cells on the plastic bottom of the flask in the presence of the beads. The roller bottle was incubated overnight at 37° C., after which 100 mL additional medium was added to the roller bottle and the rotation of the roller bottle was initiated (rotation rate=one turn/15 sec.).

To feed the cells, an aliquot of medium was removed and replaced by fresh medium, adjusted to the correct pH with $CO_2$ gassing. The cells were fed every 48 hours.

Experimental Design

An eight-day animal trial was conducted with two groups of ten animals each. The wound dressings (see below) were changed every other day starting on day 0. Wound area measurements and photographs were obtained at days 0, 2, 4, 6, and 8.

All surgical procedures were performed under sterile conditions inside a laminar flow hood. Five-week old, female Nu/J mice (Jackson Labs) were used. Nu/J mice contain a recessive mutation found on chromosome 11 and are athymic (T-cell deficient). The mice have a reduced lymphocyte count comprised almost entirely of B-cells, a normal IgM response to thymus-independent antigens, a poor response to thymus antigens, increased macrophage and NK cell activity, and increased susceptibility to infection. Nu/J mice do not reject allogeneic and xenogeneic skin and tumor grafts.

The mice were anesthetized with metofane (Mallinckrodt Veterinary) and prepped with ethanol. Using fine surgical scissors, a full thickness surgical wound approximately 80 $mm^2$ in area was created on the backs of the mice (the depth of the wound could be measure through the panniculus carnosis, but mouse skin is so thin so it was not used as an indicator here). The wound dressings (see below) were secured to the cephalad end of the wound with a surgical staple. Thereafter, each mouse was returned to its biohazard containment cage.

On days 2, 4, 6 and 8, the animals were returned to the laminar flow hood for removal of the staple and replacement of the bag. The animals were lightly restrained while area and photographic measurements were obtained (described below). The dressing was replaced and secured; all dressing changes were performed using sterile technique without general anesthesia.

Wound Dressing

The wounds were dressed either with human cultured keratinocytes grown on beads (keratinocytes/beads) in a DELNET™ bag (P530 Natural; AET, Inc.) or a DELNET™ bag alone (P530 Natural; AET, Inc.); the DELNET™ bags were approximately square (about 23 mm×25 mm). The seams of the bags were prepared with an Impulse heat sealing unit (American International Electric Co.). Prior to application on the mice, the DELNET™ bags were gas sterilized with ethylene oxide and placed in a sterile package. A BANDAID™ (3M Healthcare) covered the DELNET™ bags and was secured with surgical staples (Richard-Allen, Inc). The bag was stapled to the bandaid, and the bandaid was stapled to the mouse.

The bag and bead assembly was performed in a tissue culture hood. Inside a laminar flow hood, the keratinocytes/bead suspension was transferred to the DELNET™ bag with a glass pipet. Approximately 250 μL of the keratinocyte/bead suspension was placed in the bag. After the beads were loaded into the bag, the final seam was made with a surgical needle holder heated in a glass bead sterilizer. The DELNET™ bag containing the keratinocytes/bead suspension is referred to as "beads/bag," while the DELNET™ bag without the beads is referred to as "bag." The bags and beads/bags were placed in the complete MCDB 153 medium described above after they were loaded and heat sealed.

Measurement of Wound Area

Total area of mouse wounds was performed as previously described [Schwarz et al., Wound Repair and Regeneration 3:204–212 (1995)]. Briefly, the area of the wound was traced on transparency film (Apollo, Ronkonkoma, N.Y.) with a fine marker. The transparency film was photocopied onto plain paper and subsequently scanned into a PIC file with a Lightning Scan Pro 256 hand scanner (Thunderware). Tissue area was calculated with non-rectangular area analysis used by NIH image 1.58, and the data was expressed as millimeters squared. Mean and standard deviation were calculated using Statworks software (a statistically significant difference was $p<0.05$).

B. Experimental Results

Table 2 presents wound tissue area ($mm^2$) at baseline (day 0) and at days 2, 4, 6, and 8 for each mouse which received bags containing keratinocyte-coated beads (beads/bags); the reduction in size of the wound as a percentage of the original wound size for each mouse is also set forth. Analogous data for the mice that received bags alone is presented in Table 3.

Table 4 presents the cumulative data for i) the beads/bags mice and ii) the bags only mice.

TABLE 2

| | Mouse 1 | | Mouse 2 | | Mouse 3 | | Mouse 4 | | Mouse 5 | |
|---|---|---|---|---|---|---|---|---|---|---|
| ID | $mm^1$ | % Smaller | $mm^2$ | % Smaller | $mm^2$ | % Smaller | $mm^2$ | % Smaller | $mm^2$ | % Smaller |
| Day 0 | 117.02 | | 66.29 | | 89.89 | | 69.9 | | 103.82 | |
| Day 2 | 92.44 | 21 | 90.87 | 0 | 63.13 | 30 | 51.34 | 27 | 180.56 | 0 |
| Day 4 | 70.31 | 40 | 68.81 | 0 | 31.6 | 65 | 40.65 | 42 | 85.68 | 17 |
| Day 6 | 80.87 | 31 | 54.21 | 18 | 32.73 | 64 | 39.24 | 44 | 89.76 | 14 |
| Day 8 | 50.05 | 57 | 37.18 | 44 | 26.73 | 70 | 31.95 | 54 | 58.58 | 44 |
| | Mouse 6 | | Mouse 7 | | Mouse 8 | | Mouse 9 | | Mouse 10 | |
| ID | $mm^2$ | % Smaller | $mm^2$ | % Smaller | $mm^2$ | % Smaller | $mm^2$ | % Smaller | $mm^2$ | % Smaller |
| Day 0 | 61.61 | | 58.81 | | 80.08 | | 78.02 | | 65.5 | |
| Day 2 | 40.97 | 34 | 49.84 | 15 | 111.31 | 0 | 103.48 | 0 | 79.92 | 0 |
| Day 4 | 28.5 | 54 | 21.11 | 64 | 77.31 | 3 | 48.44 | 38 | 55.03 | 16 |
| Day 6 | 23.53 | 62 | 15.89 | 73 | 61.27 | 23 | 41.87 | 46 | 60.73 | 7 |
| Day 8 | 10.31 | 83 | 12.48 | 79 | 29.55 | 63 | 33.69 | 57 | 57.29 | 13 |

TABLE 3

| | Mouse 11 | | Mouse 12 | | Mouse 13 | | Mouse 14 | | Mouse 15 | |
|---|---|---|---|---|---|---|---|---|---|---|
| ID | $mm^2$ | % Smaller | $mm^2$ | % Smaller | $mm^2$ | % Smaller | $mm^2$ | % Smaller | $mm^2$ | % Smaller |
| Day 0 | 49.58 | | 87.16 | | 40.29 | | 90.81 | | 55.23 | |
| Day 2 | 71.23 | 0 | 160.23 | 0 | 45.5 | 0 | 201.15 | 0 | 61.55 | 0 |
| Day 4 | 51.6 | 0 | 78.68 | 10 | 33.21 | 18 | 156.42 | 0 | 52.19 | 6 |
| Day 6 | 26.48 | 47 | 52.24 | 40 | 27.95 | 31 | 92.19 | 0 | 36.61 | 34 |
| Day 8 | 33.84 | 32 | 52.4 | 40 | 15.19 | 62 | 59.15 | 35 | 30.61 | 45 |
| | Mouse 16 | | Mouse 17 | | Mouse 18 | | Mouse 19 | | Mouse 20 | |
| ID | $mm^2$ | % Smaller | $mm^2$ | % Smaller | $mm^2$ | % Smaller | $mm^2$ | % Smaller | $mm^2$ | % Smaller |
| Day 0 | 120.42 | | 59.11 | | 120.15 | | 78.29 | | 55.44 | |
| Day 2 | 90.26 | 25 | 151.4 | 0 | 151.4 | 0 | 114.18 | 0 | 89.89 | 0 |
| Day 4 | 59.84 | 50 | 124.81 | 0 | 124.81 | 0 | 138.73 | 0 | 66.58 | 0 |
| Day 6 | 47.11 | 61 | 92.94 | 23 | 92.94 | 23 | 92.39 | 0 | 59.6 | 0 |
| Day 8 | 26.95 | 78 | 90.71 | 35 | 78.32 | 35 | 65.52 | 16 | 38.79 | 30 |

TABLE 4

Day 0 Size (mm²)

|  | | | | | | Mean | 79.09 |
|---|---|---|---|---|---|---|---|
|  | | Beads/Bags | | | | SD | 19.2 |
|  | | | | | | Mean | 75.64 |
|  | | Bags Only | | | | SD | 28.64 |
|  | Day 2 | | Day 4 | | Day 6 | | Day 8 |
| % Smaller | Beads/Bags | Bags Only | Beads/Bags | Bags Only | Beads/Bags | Bags Only | Beads/Bags | Bags Only |
| Mean | 12.7 | 2.5 | 33.9 | 8.4 | 38.2 | 26.6 | 56.4 | 37.3 |
| Std Deviation | 14.29 | 7.9 | 23.82 | 15.83 | 23.06 | 22.62 | 20.12 | 21.78 |
| Significance (<0.05) | p <0.027 | | p <0.008 | | p <0.19 | | p <0.05 | |

As indicated by the data in Tables 2–4, the beads/bags showed a statistically significant difference in wound healing (i.e., a reduction in wound area) at day 2 compared to the bags alone (see Table 4, $p<0.027$). At day 4, the beads/bag (Table 2 1) treated mouse wounds had a significant reduction in wound area compared to the mouse wounds in the bags alone (Table 3), as indicated by the significance level ($p<0.008$) in Table 4. At day 6, there was no significant difference in wound healing between the two groups (see Table 3, $p<0.16$). However, at day 8, there was again a statistically significant reduction in the wound area in the beads/bag group (Table 2) compared to the bags alone group (Table 3) (see Table 4, $p<0.05$).

The experiments of this example show that cultured human keratinocytes grown on a macroporous microcarriers (beads/bag) promote wound healing. The mouse model used is predicative that human keratinocytes grown on a macroporous microcarriers contained in bags will enhance wound healing in humans.

EXAMPLE 2

The experiments of this example demonstrate that human culture keratinocytes grown on macroporous microcarriers and contained in a porous enclosure that is then covered with a wound dressing material improve healing in surgically created wounds in mice.

A. Experimental Methodology

The experiments of this example were performed as described in Example 1, with the following exceptions. The group of mice that received the keratinocyte-coated CYTOLINE 1™ macroporous microcarrier beads (Pharmacia Biotech) (i.e., the beads/bags group) comprised five animals, while the group that received only the bags (i.e., the bags only group) comprised four animals. (They are labelled 2 to 5 because Mouse 1 expired during anesthesia.) In this example the bags from both the beads/bags group and the bags only group were covered with a polyurethane film dressing (TEGADERM™, 3M Health Care, St. Paul, Minn.) with a cellophane product.

More specifically, the wounds were dressed either with human cultured keratinocytes grown on beads (keratinocytes/beads) in a DELNET™ bag (P530 Natural; AET, Inc.) or a DELNET™ bag alone (P530 Natural; AET, Inc.). Thereafter, the bags were covered with a TEGADERM™ dressing which, in turn, was covered with a BAN-DAID™ (3M Healthcare). The bags were stapled to the mouse.

B. Experimental Results

Table 5 presents wound tissue area (mm²) at baseline (day 0) and at days 2, 4, 6, and 8 for each mouse which received bags containing keratinocyte-coated beads (beads/bags); the reduction in size of the wound as a percentage of the original wound size for each mouse is also set forth. Analogous data for the mice that received bags alone is presented in Table 6.

Table 7 presents the cumulative data for i) the beads/bags mice and ii) the bags only mice.

TABLE 5

|  | Mouse 2 | | Mouse 3 | | Mouse 4 | | Mouse 5 | | Mouse 6 | |
|---|---|---|---|---|---|---|---|---|---|---|
| ID | mm² | % Smaller | mm² | % Smaller | mm² | % Smaller | mm² | % Smaller | mm² | % Smaller |
| Day 0 | 182.41 | | 132.88 | | 155.53 | | 173.76 | | 164.24 | |
| Day 2 | 162.43 | 11 | 168.57 | 0 | 157.02 | 0 | 190.51 | 0 | 216.66 | 0 |
| Day 4 | 136.73 | 25 | 122.37 | 8 | 96.69 | 38 | 164.7 | 6 | 136.72 | 17 |
| Day 6 | 74.71 | 59 | 89.91 | 33 | 49.66 | 68 | 25 | 86 | 25 | 85 |
| Day 8 | 13.19 | 93 | 10.78 | 92 | 4.59 | 97 | 18.24 | 90 | 27.87 | 83 |

TABLE 6

|  | Mouse 7 | | Mouse 8 | | Mouse 9 | | Mouse 10 | |
|---|---|---|---|---|---|---|---|---|
| ID | mm² | % Smaller | mm² | % Smaller | mm² | % Smaller | mm² | % Smaller |
| Day 0 | 134.14 | | 198.31 | | 124.1 | | 229.96 | |
| Day 2 | 151.4 | 0 | 170.21 | 0 | 166.42 | 0 | 203.36 | 0 |

TABLE 6-continued

|  | Mouse 7 | | Mouse 8 | | Mouse 9 | | Mouse 10 | |
| --- | --- | --- | --- | --- | --- | --- | --- | --- |
| ID | $mm^2$ | % Smaller | $mm^2$ | % Smaller | $mm^2$ | % Smaller | $mm^2$ | % Smaller |
| Day 4 | 206.34 | 0 | 204.39 | 0 | 160.69 | 0 | 193.03 | 16 |
| Day 6 | 112.29 | 22 | 121.92 | 39 | 117.33 | 5 | 64.92 | 22 |
| Day 8 | 16.86 | 88 | 53.45 | 73 | 61.36 | 51 | 59.3 | 74 |

TABLE 7

| Day 0 Size ($mm^2$) | | | | | | | | |
| --- | --- | --- | --- | --- | --- | --- | --- | --- |
| Cells/Bags | | | | | Mean | | 155.76 | |
| | | | | | SD | | 22.47 | |
| Bags Only | | | | | Mean | | 171.16 | |
| | | | | | SD | | 50.9 | |
| | Day 2 | | Day 4 | | Day 6 | | Day 8 | |
| % Smaller | Beads/Bags | Bags Only | Beads/Bags | Bags Only | Beads/Bags | Bags Only | Beads/Bags | Bags Only |
| Mean | 2.2 | 0 | 18.8 | 0 | 66.2 | 22 | 91 | 71.5 |
| StdDeviation | 4.9 | 0 | 13.1 | 0 | 21.8 | 13.8 | 5.1 | 15.2 |
| Significance (<0.05) | $p < 0.407$ | | $p < 0.026$ | | $p < 0.019$ | | $p < 0.030$ | |

As indicated by the data in Tables 5–7, the beads/bags demonstrated a statistically significant difference in wound healing (i.e., a reduction in wound area) at day 4 compared to the bags alone (see Table 7, $p<0.026$). The statistically significant difference in wound healing between the two groups was maintained on days 6 and 8 ($p<0.010$ and $p<0.030$, respectively).

Comparison of the data in Table 7 to that in Table 4 (Example 1) indicates that the wound dressings without TEGADERM™ begin to contract earlier than those with TEGADERM™. More specifically, the wounds of the beads/bags animals treated without TEGADERM™ were 12.7% smaller by day 2 and 33.9% smaller by day 4, while the wounds of the beads/bags animals treated with TEGADERM™ were 2.2% and 18.8% smaller on the same days. However, the size of the wounds of the beads/bags animals treated with TEGADERM™ became smaller than those treated without TEGADERM™ on days 6 and 8. While an understanding of the mechanism for this effect is not required in order to practice the present invention, it is believed to be due, in part, to the ability of the TEGADERM™ to keep the wounds moist.

The experiments of this example indicate that the systems and methods of the present invention can be practiced in combination with conventional wound healing means and procedures.

Based upon the preceding discussion and experimental materials, it should be clear that the present invention provides effective and efficient systems and methods for wound healing, especially healing of chronic wounds. The devices and methods may be used alone or in combination with other means traditionally employed in wound healing.

We claim:

1. A method for treating a wound, comprising:
    a) providing: i) keratinocytes on a solid support, ii) an enclosure comprising mesh material having pores, and iii) a subject having a least one wound;
    b) placing said keratinocyte-containing solid support into said enclosure so as to produce a keratinocyte-containing enclosure;
    c) sealing said enclosure to produce a sealed keratinocyte-containing enclosure, said pores being too small to permit said keratinocytes on said solid support to cross said mesh material;
    d) positioning said sealed keratinocyte-containing enclosure in the wound of said subject under conditions such that the healing of the wound is promoted; and
    e) removing said sealed keratinocyte-containing enclosure from said wound after wound healing is promoted.

2. The method of claim 1, wherein said solid support is beads and said beads are macroporous.

3. The method of claim 2, wherein said beads are coated with collagen.

4. The method of claim 1, wherein said mesh material comprises polyester.

5. The method of claim 1, wherein said enclosure comprises a biocompatible membrane.

6. The method of claim 1, further comprising covering said sealed keratinocyte-containing enclosure after positioning in step (c) in said wound with a dressing, and removing said dressing with said sealed keratinocyte-containing enclosure in step (e).

* * * * *

UNITED STATES PATENT AND TRADEMARK OFFICE
CERTIFICATE OF CORRECTION

| | | |
|---|---|---|
| PATENT NO. | : 5,972,332 | Page 1 of 1 |
| APPLICATION NO. | : 08/840804 | |
| DATED | : October 26, 1999 | |
| INVENTOR(S) | : Riley S. Rees et al. | |

It is certified that error appears in the above-identified patent and that said Letters Patent is hereby corrected as shown below:

At Column 1, beginning at line 5, insert the following paragraph:

--STATEMENT REGARDING FEDERALLY SPONSORED RESEARCH OR DEVELOPMENT

This invention was made with government support under a Merit Review Grant from the United States Veterans Administration. The government has certain rights in the invention.--

Signed and Sealed this

Twenty-fifth Day of May, 2010

David J. Kappos
*Director of the United States Patent and Trademark Office*